United States Patent
Beumer et al.

(10) Patent No.: US 9,944,585 B2
(45) Date of Patent: *Apr. 17, 2018

(54) FLAVOR AND FRAGRANCE FORMULATION (V)

(71) Applicant: DSM IP ASSETS B.V., Heerlen (NL)

(72) Inventors: Raphael Beumer, Basel (CH); Johannes Tschumi, Basel (CH); Michael Gressly, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/431,873

(22) PCT Filed: Oct. 7, 2013

(86) PCT No.: PCT/EP2013/070833
§ 371 (c)(1),
(2) Date: Mar. 27, 2015

(87) PCT Pub. No.: WO2014/056850
PCT Pub. Date: Apr. 17, 2014

(65) Prior Publication Data
US 2015/0259273 A1    Sep. 17, 2015

(30) Foreign Application Priority Data

Oct. 8, 2012 (EP) .................... 12187650

(51) Int. Cl.

| | | |
|---|---|---|
| *C07C 53/126* | (2006.01) | |
| *A61K 8/37* | (2006.01) | |
| *A61Q 13/00* | (2006.01) | |
| *C11B 9/00* | (2006.01) | |
| *C11D 3/50* | (2006.01) | |
| *A61L 9/01* | (2006.01) | |
| *A61Q 5/02* | (2006.01) | |
| *A61Q 5/12* | (2006.01) | |
| *A61Q 15/00* | (2006.01) | |
| *A61Q 19/10* | (2006.01) | |
| *C11D 3/20* | (2006.01) | |
| *A23L 27/20* | (2016.01) | |

(52) U.S. Cl.
CPC ........ *C07C 53/126* (2013.01); *A23L 27/2028* (2016.08); *A61K 8/37* (2013.01); *A61L 9/01* (2013.01); *A61Q 5/02* (2013.01); *A61Q 5/12* (2013.01); *A61Q 13/00* (2013.01); *A61Q 15/00* (2013.01); *A61Q 19/10* (2013.01); *C11B 9/0019* (2013.01); *C11D 3/2093* (2013.01); *C11D 3/50* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2008/0096791 | A1* | 4/2008 | Behan | ........................ A61L 9/01 512/27 |
| 2015/0246868 | A1* | 9/2015 | Beumer | ................... A61K 8/37 424/65 |

FOREIGN PATENT DOCUMENTS

| | | |
|---|---|---|
| EP | 0 269 999 | 6/1988 |
| GB | 810 748 | 3/1959 |
| JP | 55-36417 | * 3/1980 |
| WO | WO 2008/050086 | 5/2008 |
| WO | WO 2009/124888 | 10/2009 |

OTHER PUBLICATIONS

Uruma: Syntheses and odors of dimethyloctanols, Kisarazu Kogyo Koto Senmon Gakko Kiyo, vol. 17, pp. 57-62, 1984.*
International Search Report for PCT/EP2013/070833 dated Feb. 3, 2014, 2 pages.

* cited by examiner

*Primary Examiner* — Hong Yu
(74) *Attorney, Agent, or Firm* — Nixon & Vanderhye P.C.

(57) ABSTRACT

The present invention relates to the use of a specific organic compound as flavor and fragrance material. Furthermore the invention relates to flavor and fragrance formulations comprising such a specific organic compound.

6 Claims, No Drawings

FLAVOR AND FRAGRANCE FORMULATION (V)

This application is the U.S. national phase of International Application No. PCT/EP2013/070833, filed 7 Oct. 2013, which designated the U.S. and claims priority to EP Patent Application No. 12187650.2, filed 8 Oct. 2012, the entire contents of each of which are hereby incorporated by reference.

The present invention relates to the use of a specific organic compound as flavor and fragrance material. Furthermore the invention relates to flavor and fragrance formulations comprising such a specific organic compound.

In the flavor and fragrance industry there is always a need and demand for compounds that enhance, modify, improve or otherwise positively influence an odor note and therefore give perfumers or other persons the ability to create new fragrances for perfumes, colognes, personal care products, household products or any other products, which comprise flavor and fragrance materials.

Surprisingly it was found that the compound of formula (I) is very useful as flavor and fragrance material.

Therefore the present invention is related to the use of a compound of formula (I)

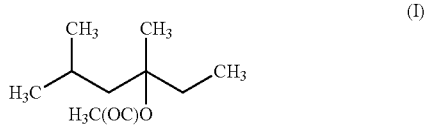

as flavor and fragrance material.

The compound of formula (I) may be used as such or in combination with other compounds which are known as flavor and fragrance material.

Such other compounds which are known as flavor and fragrance material include all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in flavor fragrance formulations, for example, carrier materials, and other auxiliary agents commonly used in the art.

The flavor and fragrance material of the present invention is used in a flavor and fragrance formulation.

Such a flavor and fragrance formulation comprises other ingredients.

The flavor and fragrance formulation according to the present invention can be in any form. Usually it is in a solid, gel-like or liquid (or a combination thereof) form. It can also be in an encapsulated form (i.e. a liquid formulation encapsulated by a suitable matrix material).

Therefore the present invention also relates to flavor and fragrance formulations comprising
(i) compound of formula (I)

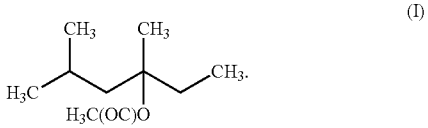

When the compound of formula (I) is used in a flavor and fragrance formulation, then the amount thereof is in the range of 0.0001-10 weight-% (wt-%), related to the total weight of the flavor and fragrance formulation. Preferred is an amount in the range of 0.01-5 wt-%.

Therefore the present invention relates to liquid flavor and fragrance formulations comprising
(i) 0.0001-10 wt-% (preferably 0.01-5 wt-%), related to the total weight of the flavor and fragrance formulation of compound of formula (I).

The flavor and fragrance formulations according to the present invention can comprise further ingredients (=auxiliary compounds), such as any further perfuming compounds solvents, adjuvants, thickeners, surface active agents, pigments, extenders, rheology modifiers, dyestuffs, antioxidants, fillers and the like.

Many flavor and fragrance formulations are in a liquid form (like a perfume, cologne, etc.). Therefore, for such liquid formulation a (diluent) solvent is present.

Such common diluents are i.e. dipropyleneglycol, isopropylmyristate, triethylcitrate and alcohols (such as ethanol).

Further examples of fine perfumery are Eau de perfume, Eau de Toilette, Eau de Cologne and Splash Cologne. Fine perfumery products are commonly based on an alcoholic solution as diluent. However fine perfumery products using an oil or wax as diluent are also included within the meaning of the present invention. The compounds can be employed in widely varying amounts, depending upon the specific application and on the nature and quantity of other odorant ingredients.

When used in a (fine) perfume, the amount is usually between 0.01-10 wt-%, based on the total weight of the (fine) perfume.

However, these values and ranges are given only by way of example, since the experienced perfumer may also achieve effects or may create novel accords with lower or higher concentrations.

Furthermore the present invention relates to liquid flavor and fragrance formulations comprising
(i) compound of formula (I), and
(ii) at least one diluent chosen from the group consisting of dipropyleneglycol, isopropylmyristate, triethylcitrate and alcohols (such as ethanol), and optionally
(iii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to solid flavor and fragrance formulations comprising
(i) compound of formula (I) and
(ii) at least one auxiliary compound selected from the group consisting of perfuming compounds solvents, adjuvants, thickeners, surface active agents, pigments, extenders, rheology modifiers, dyestuffs, antioxidants and fillers.

The compound of formula (I) may be used in a broad range of flavor and fragrance formulations, e.g. in any field of fine and functional perfumery, such as perfumes, air care products, household products, laundry products, body care products and cosmetics.

The compound as described hereinabove may be employed in a flavor and fragrance formulation simply by directly mixing the compound of formula (I), a mixture thereof, or a fragrance composition with the other ingredients used in the final product, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or it may be chemically bonded to substrates, which are adapted to release the fragrance molecule upon application of an external stimulus such as light, enzyme, or the like, and then mixed with the other ingredients used in the final product.

Thus, the invention additionally provides a method of manufacturing a flavor and fragrance formulation, comprising the incorporation of compound of formula (I), as a fragrance ingredient, either by directly admixing the compound to the other ingredients used in the final product or by admixing a fragrance composition comprising compound of formula (I), which may then be mixed with the other ingredients used in the final product, using conventional techniques and methods.

Through the addition of an olfactory acceptable amount of the compound of the present invention as hereinabove described, or a mixture thereof, the odor notes of a consumer product base will be improved, enhanced or modified.

Thus, the invention furthermore provides a method for improving, enhancing or modifying a consumer product (=final product) base by means of the addition thereto of an olfactorily acceptable amount of the compound of formula (I).

In the context of the present invention the olfactory effective amount is to be understood as the amount of the compound of formula (I) in a flavor and fragrance formulation will contribute to its particular olfactory characteristics, but the olfactory effect of the flavor and fragrance formulation will be the sum of the effects of each of the perfumes or fragrance ingredients. Thus the compound of the invention can be used to alter the aroma characteristics of the flavor and fragrance formulation, or by modifying the olfactory reaction contributed by another ingredient in the composition. The amount will vary depending on many factors including other ingredients, their relative amounts and the effect that is desired.

As used herein, "consumer product (=final product)" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body care products, e.g. shampoo, shower gel; air care products and cosmetics, e.g. deodorant, vanishing creme. This list of products is given by way of illustration and is not to be regarded as being in any way limiting.

The compound of formula (I) may be prepared using methods known to the person skilled in the art of organic synthesis.

The invention is now further illustrated in the following non-limiting examples.

EXAMPLES

The compound was evaluated by a panel of four persons for their intensity whereby a range of 1 to 10 was used (1=very low intensity; 10=very high intensity). Furthermore these four persons also described the odor of the compound. The tenancy was evaluated by one person after 3, 6, 8, 24, 48, 72 and 96 hours. For such evaluations a piece of paper was immersed in each single liquid compound as such.

Example 1: Olfactory Properties of the Compound of Formula I

Odour description: fresh; juicy; woody; mint; camphor.
Intensity: 6.
Tenancy: 3-6 hours.

The invention claimed is:

1. A flavor and fragrance formulation comprising a flavor and fragrance effective amount of 0.0001-10 wt-%, based on total weight of the flavor and fragrance formulation, of a compound of formula (I):

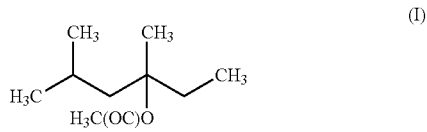

which is sufficient to impart a mint or camphor flavor and fragrance to the formulation.

2. The flavor and fragrance formulation according to claim 1, wherein the flavor and fragrance formulation is a solid, a gel or a liquid.

3. A product which comprises the flavor and fragrance formulation according to claim 1.

4. The product according to claim 3, wherein the product selected from perfumes, air care products, household products, laundry products, body care products and cosmetic products.

5. A method of improving, enhancing or modifying a flavor and fragrance formulation which comprises adding to the flavor and fragrance formulation a flavor and fragrance effective amount of a compound of formula (I):

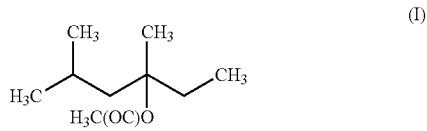

which is sufficient to impart a mint or camphor flavor and fragrance to the formulation.

6. The method according to claim 5, wherein the compound of formula (I) is added to the flavor and fragrance formulation in an amount comprising 0.0001-10 wt-%, based on total weight of the flavor and fragrance formulation.

* * * * *